United States Patent [19]

Revis

[11] Patent Number: 5,688,766

[45] Date of Patent: Nov. 18, 1997

[54] ANTICARIES COMPOSITIONS

[76] Inventor: George Joe Revis, The Procter & Gamble Company, 11450 Grooms Rd., Cincinnati, Ohio 45242-1434

[21] Appl. No.: 538,165

[22] Filed: Aug. 23, 1995

Related U.S. Application Data

[63] Continuation of Ser. No. 334,891, Nov. 4, 1994, abandoned, which is a continuation of Ser. No. 158,536, Dec. 2, 1993, abandoned, which is a continuation-in-part of Ser. No. 998,214, Dec. 30, 1992, abandoned.

[51] Int. Cl.$^6$ .......................... A61K 38/00; C07K 14/00
[52] U.S. Cl. .......................... 514/12; 530/835; 530/866
[58] Field of Search ....................... 514/12, 835; 530/866

[56] References Cited

PUBLICATIONS

Isemura et al., FEBS Letters, vol. 198, #1, Mar. pp. 145–149 (1986).
Al–Hashimi and M. Lavine, Arch Oral. Biol., vol. 34 No. 4, pp. 289–294 (1989).
Mandel, Comp. Contin. Dental. Educ., Suppl. 13, pp. 5476–5481 ( ).
Mandel, "Impact of Saliva on Dental Caries"; Compend Contin. Educ. Dent.; Suppl. No. 13; pp. S476–S481.
W. M. Rathman et al.; "Comparison of a salivary 14 kD protein displaying cysteine proteinase inhibitory activity with other salivary cystatins"; J. Biol. Buccale; vol. 18, pp. 9 a 18; 1990.
C. W. I. Douglas, "Characterization of the α–amylase receptor of *Streptococcus gordonii*"; J. Dent. Res.; vol. 69 (11); pp. 1746–1752; Nov. 1990.
W. M. Rathman, et al.; "Characterization of monoclonal antibodies to human salivary (glyco) proteins. Cellular localization of mucin, cystatin–like 14 kD protein and 20 kD glycoprotein in the human submandibular gland"; J. Biol Buccale; vol. 18; pp. 19 a 27; 1990.
Phyllis A. Shaw, et al.; "Expression and induction by β–adrenergic agonists of the cystatin S gene in submandibular glands of developing rats"; Biochem. J.; vol. 265; pp. 115–120; 1990.
Irwin D. Mandel, DDS; "The role of saliva in maintaining oral homeostasis"; JADA; vol. 119; pp. 298–304; Aug., 1989.
Gurrinder S. Bedi; "Amino Acid Sequence of an Inducible Cysteine Proteinase Inhibitor (Cystatin) from Submandibular Glands of Isoproterenol–Treated Rats"; Archives of Biochemistry and Biophysics; vol. 273, No. 1; pp. 245–253; Aug. 15, 1989.
L. M. Sabatini et al.; "Tissue Distribution of RNAs for Cystatins, Histatins, Statherin, and Proline–rich Salivary Proteins in Humans and Macaques"; J. Dent. Res.; vol. 68(7); pp. 1138–1145; Jul., 1989.
Evelyn T. Bell et al.; "Interaction of terbium and calcium with chicken cystatin"; Archives of Biochemistry and Biophysics; vol. 271, No. 2; pp. 359–365; Jun., 1989.

G. S. Bedi; "The effects of autonomic drugs on the concentration of kallikrein–like proteases and cysteine–proteinase inhibitor (cystatin) in rat whole saliva"; J. Dent. Res.; vol. 70(5); pp. 924–930; May, 1991.
I. Al–Hashimi et al.; "Characterization of in vivo salivary–derived enamel pellicle"; Archs Oral Biol.; vol. 34(4); pp. 289–295; 1989.
W. M. Rathman et al.; "Isolation and characterization of three non–mucinous human salivary proteins with affinity for hydroxyapatite"; J. Biol. Buccale.; vol. 17; pp. 199 a 208; 1989.
I. Al–Hashimi et al.; "Purification, Molecular cloning, and sequencing of salivary cystatin SA–I"; The Journal of Biological; vol. 263(19); pp. 9381–9387; Jul. 5, 1988.
Phyllis A. Shaw et al.; "Cloning and sequencing of cDNA encoding a rat salivary cysteine proteinase inhibitor inducible by β–adrenergic agonists"; The Journal of Biological Chemistry; vol. 263(34); pp. 18133–18137; Dec. 5, 1988.
David H. Hawke et al.; "Identification of a long form of cystatin from human saliva by rapid microbore HPLC mapping"; Biochemical and Biophysical Research Communications; vol. 145(3); pp. 1248–1253; Jun. 30, 1987.
Satoko Isemura et al.; "Characterization of a new cysteine proteinase inhibitor of human saliva, cystatin SN, which is immunologically related to cystatin S"; J. Biochem.; vol. 198(1); pp. 145–149; Mar., 1986.
Mei–Sheng Ruan et al.; "Quantitative, immunochemistry of salivary proteins adsorbed in vitro to enamel and cementum from caries–resistant and caries–susceptible human adults"; Archs oral Biol.; vol. 31(9); pp. 597–601; 1986.
G. E. Minah et al.; "Metabolic differences between saliva from caries–active and caries–and restoration–free children"; Archs oral Biol.; vol. 31(10); pp. 633–638; 1986.
C. DiPaola et al.; "Host Proteins in dental plaques of caries–resistant versus caries–susceptible human groups"; Archs oral Biol.; vol. 29(5); pp. 353–355; 1984.
A. C. Juriaanse et al.; "Isolation and partial characterisation of three acidic proteins from human submandibular saliva"; Archs oral Biol.; vol. 24; pp. 621–625; 1979.
A. C. Juriaanse et al.; "Isolation and characterisation of the main neutral protein from human submandibular saliva"; Archs oral Biol.; vol. 24; pp. 825–828; 1979.

(List continued on next page.)

*Primary Examiner*—Cecilia J. Tsang
*Assistant Examiner*—P. L. Touzeau
*Attorney, Agent, or Firm*—Douglas C. Mohl; Mary Catherine Poland; Jacobus C. Rasser

[57] ABSTRACT

The present invention relates to oral and edible compositions intended to provide an anticaries benefit. The primary active ingredient in these compositions is a protein selected from the group consisting of cystatin S, cystatin SA, cystatin SN and mixtures thereof which are salivary proteins. Also included are fragments of the proteins which may be used in place of the total proteins.

17 Claims, No Drawings

OTHER PUBLICATIONS

Thomas F. Boat et al., "Purification and properties of the calcium–precipitable protein in submaxillary saliva of normal and cystic fibrosis subjects"; Pediat. Res.; vol. 8; pp. 531–539; 1974.

Joseph W. Mayo et al., "Protein composition of human submandibular secretions"; Archives of Biochemistry and Biophysics; vol. 161; pp. 134–145; (1974).

Anders Grubb et al.; "The disulphide bridges of human cystatin C (γ–trace) and chicken cystatin"; Elsevier Science Publishers; vol. 170(2); pp. 370–374; May 1984.

Janice M. Joneja, et al.; "Identification of transcalciferin as a major component of human parotid saliva by crossed immunoelectrophoretic mapping"; Arch. oral Biol.; vol. 27; pp. 51–58; 1982.

J. P. Shomers et al.; "Characterization of cysteine–containing phosphoproteins from human submandibular–sublingual saliva"; J. Dent. Res.; vol. 61(6); pp. 764–767; Jun. 1982.

S. M. Vratsanos et al.; "Comparative plaque acidogenesis of caries–resistant vs. caries–susceptible adults"; J. Dent. Res.; vol. 61(3); pp. 465–468; Mar. 1982.

J. P. Shomers et al.; "The isolation of a family of cysteine–containing phosphoproteins from human submandibular–sublingual saliva"; J. Dent. Res.; vol. 61(8); pp. 973–977; Aug. 1982.

J. P. Shomers et al.; "Properties of cysteine–containing phosphoproteins from human submandibular–sublingual saliva"; J. Dent. Res.; vol. 61(2); pp. 397–399; Feb. 1982.

L. C. Anderson et al.; "Salivary protein polymorphisms in caries–resistant adults"; J. Dent. Res.; vol. 61(10); pp. 1167–1168; Oct. 1982.

D. C. Abelson et al.; "The effect of saliva on plaque pH in vivo"; J. Dent. Res.; vol. 60(9); pp. 1634–1638; Sep. 1981.

R. A. Cowman et al.; "Differential utilization of proteins in saliva from caries–active and caries–free subjects as growth substrats by plaque–forming streptococci"; J. Dent. Res.; vol. 58(10); pp. 2019–2027; Oct. 1979.

Keiji Okamura et al.; "Serum proteins and secretory component in human carious dentin"; J. Dent. Res.; vol. 58(3); pp. 1127–1133; Mar. 1979.

A. Y. Balekjian et al.; "Electrophoretic patterns of parotid fluid proteins from caries–resistant and caries–susceptible individuals"; J. Dent. Res.; vol. 54(4); pp. 850–856; Jul.–Aug. 1975.

Gurrinder S. Bedi; "Purification and Characterization of an inducible cysteine proteinase inhibitor from submandibular glands of isoproterenol–treated rats"; Archives of Biochemistry and Biophysics; vol. 270(1); pp. 335–343; Apr. 1989.

# 5,688,766

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 56 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:1:

```
Ser  Ser  Ser  Lys  Glu  Glu  Asn  Arg  Ile  Ile  Pro  Gly  Gly  Ile  Tyr  Asp
  1                  5                           10                          15

Ala  Asp  Leu  Asn  Asp  Glu  Trp  Val  Gln  Arg  Ala  Leu  His  Phe  Ala  Ile
               20                           25                          30

Ser  Glu  Tyr  Asn  Lys  Ala  Thr  Glu  Asp  Glu  Tyr  Tyr  Arg  Arg  Pro  Leu
               35                           40                     45

Gln  Val  Leu  Arg  Ala  Arg  Glu  Gln
      50                      55
```

( 2 ) INFORMATION FOR SEQ ID NO:2:

( i ) SEQUENCE CHARACTERISTICS:
        ( A ) LENGTH: 38 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:2:

```
Thr Phe Gly Gly Val Asn Tyr Phe Phe Asp Val Glu Val Gly Arg Thr
 1               5                  10                  15

Ile Cys Thr Lys Ser Gln Pro Asn Leu Asp Thr Cys Ala Phe His Glu
            20                  25                  30

Gln Pro Glu Leu Gln Lys
            35
```

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:3:

```
Lys Gln Leu Cys Ser Phe Glu Ile Tyr Tyr Glu Val Pro Trp Glu Asp
 1               5                  10                  15

Arg Met Ser Leu Val Asp Ser Arg Cys Gln Glu Ala
            20                  25
```

( 2 ) INFORMATION FOR SEQ ID NO:4:

( i ) SEQUENCE CHARACTERISTICS:
        ( A ) LENGTH: 56 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:4:

```
Trp Ser Pro Gln Glu Glu Asp Arg Ile Ile Glu Gly Gly Ile Tyr Asp
 1               5                  10                  15

Ala Asp Leu Asn Asp Glu Arg Val Gln Arg Ala Leu His Phe Val Ile
            20                  25                  30

Ser Glu Tyr Asn Lys Ala Thr Glu Asp Glu Tyr Tyr Arg Arg Leu Leu
            35                  40                  45

Arg Val Leu Arg Ala Arg Glu Gln
            50                  55
```

( 2 ) INFORMATION FOR SEQ ID NO:5:

( i ) SEQUENCE CHARACTERISTICS:
        ( A ) LENGTH: 38 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:5:

```
Ile Val Gly Gly Val Asn Tyr Phe Phe Asp Ile Glu Val Gly Arg Thr
 1               5                  10                  15

Ile Cys Thr Lys Ser Gln Pro Asn Leu Asp Thr Cys Ala Phe His Glu
            20                  25                  30

Gln Pro Glu Leu Gln Lys
            35
```

(2) INFORMATION FOR SEQ ID NO:6:

(i) SEQUENCE CHARACTERISTICS:
        (A) LENGTH: 27 amino acids
        (B) TYPE: amino acid
        (C) STRANDEDNESS: unknown
        (D) TOPOLOGY: unknown (xi) SEQUENCE DESCRIPTION: SEQ ID NO:6:

```
Lys Gln Leu Cys Ser Phe Gln Ile Tyr Glu Val Pro Trp Glu Asp Arg
 1               5                  10                      15
Met Ser Leu Val Asn Ser Arg Cys Gln Glu Ala
             20              25
```

(2) INFORMATION FOR SEQ ID NO:7:

(i) SEQUENCE CHARACTERISTICS:
        (A) LENGTH: 56 amino acids
        (B) TYPE: amino acid
        (C) STRANDEDNESS: unknown
        (D) TOPOLOGY: unknown (xi) SEQUENCE DESCRIPTION: SEQ ID NO:7:

```
Trp Ser Pro Lys Glu Glu Asp Arg Ile Ile Pro Gly Gly Ile Tyr Asn
 1               5                  10                      15
Ala Asp Leu Asn Asp Glu Trp Val Gln Arg Ala Leu His Phe Ala Ile
             20              25                  30
Ser Glu Tyr Asn Lys Ala Thr Lys Asp Asp Tyr Tyr Arg Arg Pro Leu
         35              40                  45
Arg Val Leu Arg Ala Arg Gln Gln
     50              55
```

(2) INFORMATION FOR SEQ ID NO:8:

(i) SEQUENCE CHARACTERISTICS:
        (A) LENGTH: 38 amino acids
        (B) TYPE: amino acid
        (D) TOPOLOGY: unknown (xi) SEQUENCE DESCRIPTION: SEQ ID NO:8:

```
Thr Val Gly Gly Val Asn Tyr Phe Phe Asp Val Glu Val Gly Arg Thr
 1               5                  10                      15
Ile Cys Thr Lys Ser Gln Pro Asn Leu Asp Thr Cys Ala Phe His Glu
             20              25                  30
Gln Pro Glu Leu Gln Lys
         35
```

(2) INFORMATION FOR SEQ ID NO:9:

(i) SEQUENCE CHARACTERISTICS:
        (A) LENGTH: 27 amino acids
        (B) TYPE: amino acid
        (D) TOPOLOGY: unknown (xi) SEQUENCE DESCRIPTION: SEQ ID NO:9:

```
Lys Gln Leu Cys Ser Phe Glu Ile Tyr Glu Val Pro Trp Glu Asn Arg
 1               5                  10                      15
Arg Ser Leu Val Lys Ser Arg Cys Gln Glu Ser
             20              25
```

ANTICARIES COMPOSITIONS

CROSS REFERENCED TO RELATED APPLICATION

This is a continuation of application Ser. No. 08/334,891, filed on Nov. 04, 1994, now abandoned, which is a continuation of application Ser. No. 08/158,536, filed on Dec. 02, 1993, now abandoned, which is a continuation-in-part of application Ser. No. 07/998,214, filed on Dec. 30, 1992, now abandoned.

TECHNICAL FIELD

The present invention relates to oral and edible compositions containing certain salivary proteins or a fragment thereof to provide an anticaries effect.

BACKGROUND OF THE INVENTION

Dental caries is still a problem even though fluoridated water and fluoride toothpastes have reduced the incidence of caries to a very significant degree. There is interest, however, in developing products which possess the ability to reduce caries even more in the absence of fluoride or at a low fluoride ion concentration.

While there is an interest in developing and marketing products which reduce caries without reliance on a high level of fluoride ions, there have not been many reports of such approaches meeting with success. One approach reported is the use of phosphopeptides as disclosed in EPO 344,832 A1, Dec. 6, 1989 to Unilever.

The present inventors have surprisingly found that oral and edible compositions containing certain salivary proteins or a fragment thereof can reduce caries in those persons who have a tendency to develop caries.

While not wishing to be bound by theory, the anticaries efficacy of the cystatins is possibly due to their surprising ability to reduce acid production which acids contribute to caries.

It is thereof an object of the present invention to provide oral and edible compositions which contain cystatin S or cystatin SA or cystatin SN or a mixture thereof or a fragment thereof.

It is also an object of this invention to provide methods of reducing caries through the use of such compositions.

These and other objects will become more apparent from the detailed description which follows.

All percentages and ratios used herein are by weight unless otherwise indicates. Additionally, all measurements are made at 25° C. unless otherwise indicated.

SUMMARY OF THE INVENTION

The compositions of the present invention comprise an effective amount of cystatin S, cystatin SA, cystatin SN or a mixture thereof or a fragment thereof in a suitable oral or edible carrier.

The present invention further comprises the use of an effective amount of the compositions described herein to combat caries.

DETAILED DESCRIPTION OF THE INVENTION

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "edible" composition as used herein is meant a composition which in the ordinary course of usage is intentionally swallowed.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier" as used herein, is meant a suitable vehicle which can be used to apply the present composition in the oral cavity and either ingested or expectorated after use.

Cystatin S, Cystatin SA or Cystatin SN

Cystatin S is 121 residues in length with an MW=14,190. The gene responsible for the synthesis of cystatin S has three exons, I, II and III, which encode the following three amino acid sequences:

Exon I=SSSKEENRIIPGGIYDADLNDEWVQRALHF AISEYNKATEDEYYRRPLQVLRAREQ

Exon II=TFGGVNYFFDVEVGRTICTKSQPN LDTCAFHEQPELQK

Exon III=KQLCSFEIYYEVPWEDRMSLVDSRCQEA

Cystatin SA is also 121 residues in length with a MW=14,347. The gene responsible for the synthesis of cystatin SA also has three exons, I, II, and III, which encode the following three amino acid sequences:

Exon I=WSPQEEDRIIEGGIYDADLNDERVQRALH FVISEYNKATEDEYYRRLLRVLRAREQ

Exon II=IVGGVNYFFDIEVGRTICT KSQPNLDTCAFHEQPELQK

Exon III=KQLCSFQIYEVPWEDRMSLVNSRCQEA

Cystatin SN is 121 residues in length with a MW=14,311. The gene responsible for the synthesis of cystatin SN has three exons, I, II, and III, which correspond to the following three sequences:

Exon I=WSPKEEDRIIPGGIYNADLNDEWVQRAL-HFAJ SEYNKAT KDDYYRRPLRVLRARQQ

Exon II=TVGGVNYFFDVEVGRTICTKSQPNLDTCA-FHEQPELQK

Exon III=KQLCSFEIYEVPWENRRSLVKSRCQES

W=Trp,S=Ser, P=Pro,K=Lys,E=Glu,D=Asp,R=Arg,I=Ile, G=Gly,Y=Tyr, N=Asn,A=Ala, Q=Gla,T=Thr,V=Val,C=Cys, L=Leu,H=His,F=Phe

The "cystatin fragment" as that term is used herein includes any linear, cyclic or blocked polypeptide fragment greater than or equal to three residues in length or any modified polypeptide fragments of cystatin S, SA or SN having at least 75% homology to the original cystatin fragment. Examples of said fragments are:

A=WSPKEEDRII
B=KATKDDYYRRPLRVLRARQQ
C=ALHFAISEYNKATKDDYYRRPLRVLRARQQ
D=ADLNDEWVQRALHFAISEYNKATKDDYYRRP-LRVLRARQQ

Examples of modified cystatin fragments with the modification in brackets are:

E=WSP[R]
F=SSSKEE[R]RI[E]

The cystatins or a fragment thereof are used in the present compositions at any effective level. The levels are generally in the range of about 0.001% to about 5%, preferably from about 0.005% to about 1%, most preferably from about 0.01% to about 0.5%.

Acceptable Carrier

A preferred carrier composition for the active(s) of this invention are oral compositions. Such compositions include toothpastes, mouthrinses, liquid dentifrices, lozenges, chewing gums or other vehicle suitable for use in the oral cavity. Toothpastes and mouthrinses are the preferred systems.

The abrasive polishing material contemplated for use in the toothpaste compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For these reasons, they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the toothpaste compositions described herein is present at a level of from about 6% to 70%, preferably from about 15% to about 25%.

Flavoring agents can also be added to toothpaste compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in toothpastes at levels of from about 0.005% to about 2% by weight.

Toothpaste compositions can also contain emulsifying agents. Suitable emulsifying agents are those which are reasonably stable and foam throughout a wide pH range, including non-soap anionic, nonionic, cationic, zwittefionic and amphoteric organic synthetic surfactants. The preferred surfactants are those which are not anionic due to possible complexation of the cystatins which are zwitterionic with the surfactant. Many of these suitable agents are disclosed by Gieske et al. in U.S. Pat. No. 4,051,234, Sep. 27, 1977, incorporated herein by reference. The emulsifying agents are present at a level of from about 0.5% to about 2.0%.

Water is also present in the toothpastes of this invention. Water employed in the preparation of commercially suitable toothpastes should preferably be deionized and free of organic impurities. Water generally comprises from about 10% to 50%, preferably from about 30% to 50%, by weight of the toothpaste compositions herein. Thesee amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents in ane amount from 0.2% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can comprise the carrier for the agents of the present invention. Mouthwashes generally comprise from about 20:1 to about 2:1 of a water/ethyl alcohol solution or be alcohol free and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 0% to 60% (preferably 5% to 20%) ethyl alcohol, 0% to 20% (preferably 5% to 20%) of a humectant, 0% to 2% (preferably 0.01% to 1.0%) emulsifying agents, 0% to 0.5% (preferably 0.005% to 0.06%) sweetening agent such as saccharin or natural sweeteners such as stevroside 0% to 0.3% (preferably 0.03% to 0.3%) flavoring agent, and the balance water. Other optional components described herein earlier for use in toothpaste products are also useful in the mouthwash compositions.

An additional optional ingredient for use in the compositions is a soluble fluoride ion source. Such sources include sodium fluoride, stannous fluoride, sodium monofluorophosphate and are used in amounts sufficient to provide from about 10 to about 3500 ppm F–.

Still other optional ingredients include soluble pyrophosphate or phosphonates or carboxy polymers such as polyacrylic acid and methyl vinyl ether maleic anhydride as anticalculus agents. Also useful are antiplaque/gingivitis actives such as cationic materials such as chlorhexidine and cetyl pyridinium chloride, agents such as cimetidine and nonionic materials such as triclosan or triclosan monophosphate. These agents are described in the following U.S. Patents which are incorporated herein in then entirety: U.S. Pat. No. 4,515,772, May 7, 1985; U.S. Pat. No. 4,627,977, Dec. 9, 1986; and U.S. Pat. No. 5,032,386, Jul. 16, 1991.

The pH of the present compositions and/or the pH in the mouth can be any pH which is safe for the mouth's hard and soft tissues. Such pH's are generally from about 3 to about 10, preferably from about 4 to about 8.

Other acceptable oral carriers include gums, lozenges, as well as other forms. Such suitable forms are disclosed in U.S. Pat. No. 4,083,955, Apr. 11, 1978 to Grabenstetter et al. incorporated herein in its entirety by reference.

Edible compositions are also suitable for use as the carrier compositions herein. Edible compositions include many types of solid as well as liquid compositions. Such compositions include, for example, soft drinks, citrus drinks, cookies, cakes, breads among many others. Such compositions may contain sugar or another sweetener, water, flour, shortening, other fibers such as wheat, corn, barley, rye, oats, psyllium and mixtures thereof.

METHOD OF MANUFACTURE

The method of obtaining the cystatins or a fragment thereof as well as manufacturing the final compositions as is set forth below.

PREPARATION OF CYSTATIN SN, S & SA

Fresh human submandibular/sublingual saliva from caries-resistant individuals is collected on ice, 0° C. The collected saliva is made up to 50 mM Tris-HCl pH 7.5+0.1M NaCl and stirred on ice (0° C.) for 2 hours. The samples are centrifuged at 100,000×g for 20–24 hours at 4° C. to remove the mucins. The resultant supernatant is dialyzed extensively against $H_2O$ at 7° C. prior to ammonium sulfate fractionation. The 0–30% ammonium sulfate precipitate is discarded and the 30–50% ammonium sulfate precipitate is pelleted by centrifugation at 10,000×g for 15–20 minutes. The resultant pellet is extensively dialyzed against $H_2O$ at 7° C. The dissolved pellet is lyophilized and taken up in 50 mM MES pH 6.0 and injected onto a BioRad Macro-Prep High S Cation Exchange Support column (1 cm×21 cm) at a flow rate of 0.5 ml/min. The column effluent is monitored at 280 mn and the column is washed with 50 mM MES pH 6.0 until the protein coming through in the wash is eluted and the baseline has returned to normal. A gradient of 0 to 0.5M NaCl in 50 mM MES pH 6.0 at a flow rate of 1 ml/min for 30 minutes is used to elute the proteins from the colum. The individual fractions coming off the column are dialyzed extensively against $H_2O$ at 7° C. and lyophilized prior to further purification.

The combined S column wash fractions contain cystatin S+SA with only minor contamination by amylase according to the SDS-PAGE gel staining pattern and overall purity is further verified by HPLC reversed-phase chromatography.

Since the S column gradient fractions containing SN also contain significant amounts of the proline-rich proteins, cystatin SN is further purified using a batch hydroxyapatite procedure. BDH hydroxyapatite is hydrated in 25 mM Tris-HCl pH 8.0 0.1 mM $NaH_2PO_4$ overnight and extensively defined. The lyophilized S column gradient fraction (s) containing SN is taken up in 25 mM Tris-HCl pH 8.0+0.1 mM $NaH_2PO_4$ and added to the hydroxyapatite. This mixture is gently rocked at room temperature for 30 minutes, then centrifuged at 200×g for 10 minutes. The supernatant containing cystatin SN is removed and the hydroxyapatite is washed two more times with buffer and removed and combined with the first. The cystatin SN containing hydroxyapatite wash is dialyzed extensively against $H_2O$ at 7° C. and lyophilized.

Verification of the purification process is done by separation of aliquots of the column fractions using the Laemmeli SDS-PAGE gel electrophoresis. The gels are stained with 0.04% Commassie Blue R-250 and destained in 10% acetic acid to insure detection of the basic proline-rich proteins. Reversed-phase column chromatography is also used for further verification of purity. Lyophilized aliquots of the samples are dissolved in 5% Buffer B and 6 µg is injected onto a Vydac 218TP54 reversed-phase column. (Buffer A=0.1% trifluoroacetic acid in $H_2O$; Buffer B=0.08% trifluoroacetic acid in 80% acetonitrile). A linear gradient of 5% to 100% B is run at a flow rate of 1.0 ml/min over 30 minutes. The absorption profile is followed at 214 nm.

PREPARATION OF WSPKEEDRII

The above peptide was synthesized using FastMoc chemistry (Fmoc protection, HBTU/HOBt activation) on an Applied Biosystems model 430A peptide synthesizer. HMP resin (0.29 g, 0.85 m mol/g) was used in the preparation of the above peptide along with 1 m mol of each amino acid. The cycles on the synthesizer were the standard FastMoc/NMP cycles.

After the synthesis the peptide was cleaved from the resin using TFA:EDT:$H_2O$:Phenol:Thioanisole [10:0.25:0.5:0.75:0.5] for 1.5 hours at room temperature. The peptide-resin TFA mixture was filtered through a medium porosity filter and the filtrate reduced to 2 mL by rotary evaporation. This was diluted to 20 mL with $H_2O$ and washed three times with an equal volume of $Et_2O$. The aqueous layer was lyophilized overnight.

The crude peptide was analyzed by reversed phase high performance chromatography (Beckman) on a Vydac column ($C_{18}$ 5 m 300A, 4.6×250 mm) with the following gradient 0–40% B over 40 minutes (A=0.1TFA, B=99.9% $CH_3CN$, 0.1% TFA) at 1 ml per minute. After characterization (see below) the crude peptide was prepped on a Vydac column ($C_{18}$ 10 m 300A, 25×250 mm) with the above gradient at a flow of 10 ml per minute.

Both the crude and HPLC purified peptide were characterized by LCMS techniques on a SCIEX MS, the appropriate mass was determined in both cases. The resulting peptide is >95% pure by HPLC.

Definitions

Fmoc, 9-Fluorenylmethyloxycarbonyl; HBTU, (2-(H-Benzotraizol-1-yl)-1, 1, 3, 3-tetramethyluronium hexafluorophosphate; HOBt, 1-Hydroxybenzotriazole; hydrate; HMP, p-Hydroxymethylphenoxymethyl polystyrene; NMP, N-Methylpyrrolidone; TFA, Trifluoroacetic acid; EDT, 1,2-Ethanedithiol.

Industrial Applicability

The compositions of the present invention are used in a conventional manner.

The following examples further describe and demonstrate preferred embodiments within the scope of the present invention. The examples are given solely for the purpose of illustration and are not to be construed as limitations of this invention. Many variations are possible without departing from the invention's spirit and scope.

In addition to the levels and combinations of ingredients shown in these examples, others can be used which are consistent with the invention as disclosed herein.

EXAMPLE I

This is a mouthrinse which is representative of the present invention.

| Component | Wt. % |
|---|---|
| Cystatin SA | 0.05 |
| Ethanol (190 proof) | 5.500 |
| Glycerine | 5.000 |
| Flavor | 0.070 |
| POE(20) Sorbitan Monoisostearate | 0.050 |
| Sodium Saccharin | 0.050 |
| Distilled Water | qs 100.000 |

EXAMPLE II

The following is a toothpaste which is representative of the present invention.

| Component | Wt. % |
|---|---|
| Precipitated Silica Abrasive | 35.0 |
| Cystatin SN | 0.25 |
| Glycerin | 5.0 |
| Sorbitol Solution (70%) | 20.0 |
| Carboxymethyl Cellulose (0.7 D.S.) | 0.5 |
| Monosodium Orthophosphate Monohydrate (NaH$_2$PO$_4$H$_2$O) | 0.3 |
| Disodium Orthophosphate Dihydrate (Na$_2$HPO$_4$2H$_2$O) | 0.3 |
| Nonionic Surfactant | 2.3 |
| Flavor | 0.9 |
| Sodium Saccharin | 0.2 |
| Titanium Dioxide (TiO$_2$) | 0.5 |
| Speckles | 0.5 |
| Distilled Water | q.s. |
| Total | 100.0 |

EXAMPLE III

This is another mouthrinse representative of the present invention.

| Component | Wt. % |
|---|---|
| Fragment A* | 0.500 |
| Ethanol (190 proof) | 5.500 |
| Glycerine | 5.000 |
| Flavor | 0.070 |
| POE(20) Sorbitan Monoisostearate | 0.050 |
| Sodium Saccharin | 0.050 |
| Distilled Water | qs 100.000 |

*Fragment A as defined on page 6, is WSPKEEDRII.

The proteins of Examples I and III were evaluated in a microbiological assay to determine their ability to reduce acid production.

In this assay, 200 ul of bacteria were suspended in saline with an optical density (O.D.) of 0.175, and were added to 200 ul of saline containing the protein (or polypeptide) and rambled for six minutes at 8 1/2 cycles/minute at 37° C. Then 300 ul of a solution containing 11.2% sucrose, 0.9% saline and 0.21% trypticase soy broth without dextrose was added to the bacteria and the air-tight robes rambled for 2.5–4 hours when the pH was read using a micro-pH electrode.

The table below gives the concentration of the actives at which a 50% inhibition of acid production occurs relative to a negative control.

Concentration which gives a 50% reduction in acid production:

| | |
|---|---|
| Cystatin SA | $6 \times 10^{-7}$ M |
| Fragment A | $1 \times 10^{-5}$ M |

---

What is claimed:

1. A flavored oral or edible composition comprising an oral or edible carrier composition and cystatin SN or a fragment thereof or mixtures thereof, wherein when used alone or in a mixture, said cystatin or fragment thereof is present at a level of from about 0.001% to about 5%.

2. A composition according to claim 1 wherein the composition is an oral composition.

3. An oral composition according to claim 2 which is in the form of a toothpaste, mouthrinse, liquid dentifrice, chewing gum or lozenge.

4. An oral composition according to claim 3 which is in the form of a toothpaste which contains a silica dental abrasive.

5. An oral composition according to claim 4 which in addition contains a soluble fluoride ion source sufficient to provide from about 0 to about 3500 ppm F-.

6. An oral composition according to claim 5 which in addition contains from about 0 to about 10% of an emulsifying agent.

7. An oral composition according to claim 6 which in addition contains from about 0.1% to about 1% of a toothpaste binder or an antiplaque agent or an anticalculus agent or a mixture thereof.

8. An oral composition according to claim 1 which is in the form of a mouthrinse.

9. An oral composition according to claim 8 which in addition contains from about 0 to about 70% of a humectant.

10. An oral composition according to claim 9 which in addition contains from about 0 to about 10% of an emulsifier.

11. A composition according to claim 1 which is in the form of a chewing gum or lonzenge.

12. A composition according to claim 2 which is an edible composition.

13. A composition according to claim 11 which is in the form of a citrus drink, a soft drink, a cookie, cake, wafer or snack food.

14. A method of reducing caries by applying to the enamel surfaces in the mouth of an individual susceptible to caries formation an effective amount of a composition according to claim 1.

15. A method according to claim 14 wherein said composition is in the form of a toothpaste.

16. A method according to claim 15 wherein said composition is a mouthrinse.

17. A method according to claim 14 wherein said composition is an edible composition.

* * * * *

UNITED STATES PATENT AND TRADEMARK OFFICE
CERTIFICATE OF CORRECTION

PATENT NO. : 5,688,766
DATED : November 18, 1997
INVENTOR(S) : George Joe Revis

It is certified that error appears in the above-indentified patent and that said Letters Patent is hereby corrected as shown below:

Column 2, line 63, delete "C=ALHIFAISEYNKATKDDYYRRPLRVLRARQQ" and insert -- C=ALHFAISEYNKATKDDYYRRPLRVLRARQQ --

Column 3, line 63, delete "zwittefionic" and insert -- zwitterionic --

Column 5, line 1, delete "carders" and insert -- carriers --

Column 5, line 35, delete "mn" and insert -- nm --

Column 5, line 52, delete "8.0  1.0 mM" and insert -- 8.0 + 0.1 mM --

Column 8, line 24, delete "robes rambled" and insert -- tubes tumbled --

Signed and Sealed this

Fourth Day of August, 1998

*Attest:*

BRUCE LEHMAN

*Attesting Officer*   *Commissioner of Patents and Trademarks*